(12) United States Patent
Manspeizer

(10) Patent No.: US 7,553,331 B2
(45) Date of Patent: Jun. 30, 2009

(54) INTERNAL BRACE FOR DISTRACTION ARTHROPLASTY

(76) Inventor: Sheldon Manspeizer, 1 Greenridge Ave., P.O. Box 42, White Plains, NY (US) 10605

( * ) Notice: Subject to any disclaimer, the term of this patent is extended or adjusted under 35 U.S.C. 154(b) by 0 days.

(21) Appl. No.: 11/588,528

(22) Filed: Oct. 26, 2006

(65) Prior Publication Data

US 2007/0106299 A1 May 10, 2007

Related U.S. Application Data

(63) Continuation of application No. 10/841,354, filed on May 7, 2004, now abandoned.

(60) Provisional application No. 60/480,090, filed on Jun. 19, 2003.

(51) Int. Cl.
*A61F 2/38* (2006.01)

(52) U.S. Cl. .................................. 623/20.3; 606/90
(58) Field of Classification Search .............. 623/20.34, 623/20.26, 20.16, 20.36
See application file for complete search history.

(56) References Cited

U.S. PATENT DOCUMENTS

| 5,443,516 A | * | 8/1995 | Albrektsson et al. ...... 623/23.39 |
| 6,113,637 A | * | 9/2000 | Gill et al. ................. 623/17.15 |
| 6,264,696 B1 | * | 7/2001 | Reigner et al. ........... 623/20.24 |

* cited by examiner

*Primary Examiner*—Corrine M McDermott
*Assistant Examiner*—Christopher D Prone
(74) *Attorney, Agent, or Firm*—Darby & Darby P.C.

(57) ABSTRACT

A method for treating a patient suffering from osteoarthritis and an internal brace for distraction arthroplasty including femoral and tibial components which can be fixed to a patient's femur and tibia and which in combination distract or separate the knee joint without substantially hindering mobility of the knee.

7 Claims, 3 Drawing Sheets

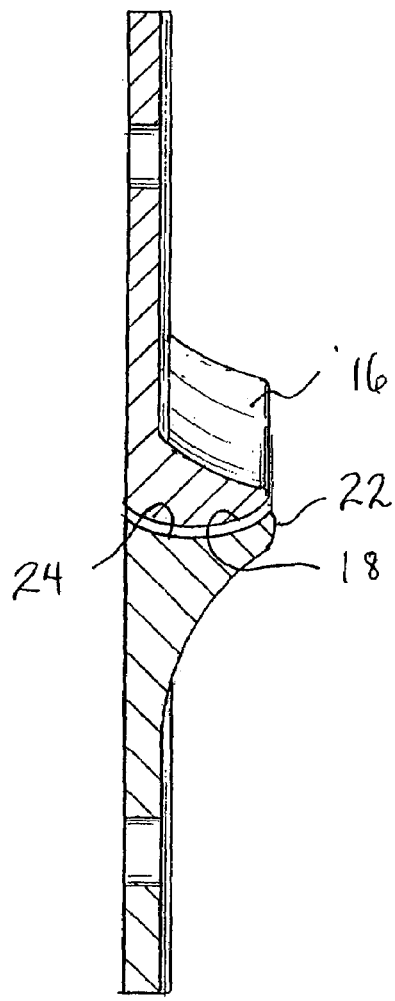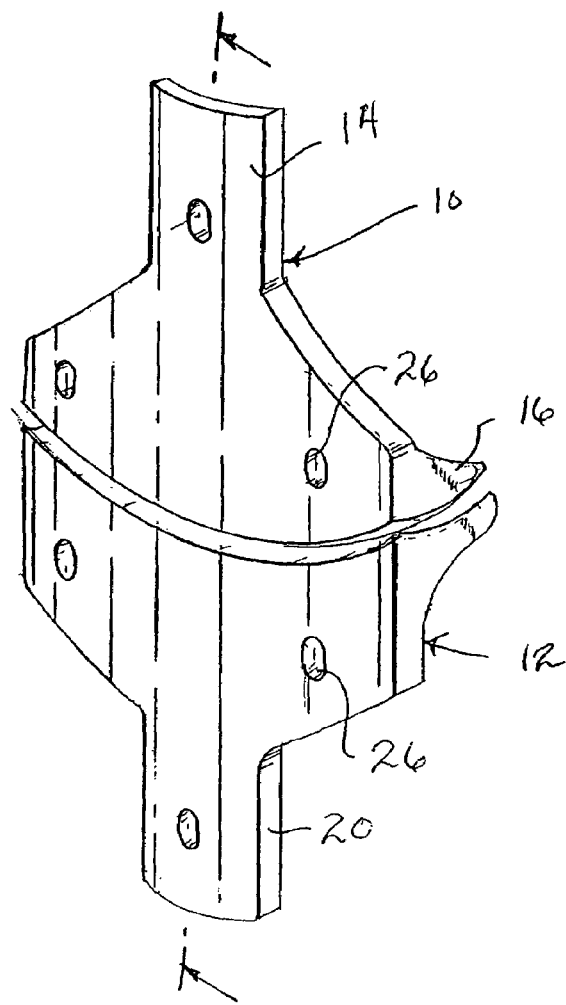
Fig. 1
Fig. 2

INTERNAL BRACE FOR DISTRACTION ARTHROPLASTY

This patent application is a continuation of U.S. patent application Ser. No. 10/841,354, filed May 7, 2004, which claims priority pursuant to 35 U.S.C. § 119 from Provisional Patent Application Ser. No. 60/480,090 entitled "Internal Brace for Distraction Arthroplasty," filed Jun. 19, 2003, the both disclosures are hereby incorporated by reference in their entirety.

This invention relates to a brace for use with patients suffering from osteoarthritis in the knee. More particularly, the invention relates to an internal brace which can be fixed to a patient's femur and tibia and which distracts or separates the knee joint without substantially hindering mobility of the knee.

BACKGROUND OF THE INVENTION

The main radiological finding of a unicompartment osteoarthritis of the knee is the loss or decrease in the articular cartilage space. The secondary findings are spur formation and/or synovitis of the knee. The articular cartilage that is lost in the knee generally occurs in either one of two ways; first in the medial joint and then extending to the patellofemoral joint and eventually to the lateral joint. When this situation occurs the patient has a varus deformity of the knee. The other situation that occurs is a loss of the lateral joint articular cartilage initially, then loss of the patellofemoral cartilage space, and eventually, loss of the medial joint compartment space. In this situation one has a valgus deformity of the knee. Present also in a primary osteoarthritis or unicompartment arthritis of the knee is loss of the meniscal space due to an extrusion of the meniscus and/or tears of the meniscus. In other words, generally there is a primary loss of the articular cartilage followed by secondary degenerative changes of the menisci.

The other situations that can occur are a primary tear of the lateral meniscus which can lead to lateral joint arthritis, or tear of the medial meniscus leading to secondary osteoarthritis of the medial joint. The latter situation often occurs in traumatic injuries in young people who later on develop osteoarthritis of the knee. In both situations, the end result is that there is a loss or decrease in either the medial or lateral joint space with associated tearing or extrusion of the medial meniscus or lateral meniscus.

There are ways to prevent or treat the collapse of the medial and lateral joint. The present techniques include a unispacer, a unicompartment knee replacement, a meniscal transplant or allograft, a high tibial osteotomy, and/or an unloading external brace. All of these techniques seek to prevent further collapse of the medial and lateral joints, i.e., they provide for decompression of the medial and lateral joints. All of these methods except for bracing have limitations in that they do not encourage replenishment or regeneration of the articular cartilage but rather replace the surface of the articular cartilage.

An object of the invention is to provide an internal brace for the medial and/or lateral joint of the knee which will prevent this process from progressing.

Another object is to provide an internal knee brace which will provide for decompression of the medial and/or lateral joints without removing or replacing articular cartilage.

A still further object of the invention is to provide an internal brace for a knee joint in which the adjacent joint surfaces are forced apart in order to give the cartilage between the surfaces a chance to regenerate.

SUMMARY OF THE INVENTION

An internal brace of the knee must provide for the rolling motion of the knee, the rotational motion of the knee, and the sagittal plane motion of the knee for flexion and extension. The knee joint includes a meniscal space that forms a triangular shape along the anterior, posterior, lateral and medial aspect of the knee. The invention provides an implantable brace for use in a knee joint which functions as a wedge in this meniscal space to distract or pry open the joint where there has been unicompartment articulate cartilage narrowing, while enabling motion of the knee both in anterior and posterior rolling motions, and providing for rotational and sagittal plane motion.

In accordance with a further aspect of the invention, the invention provides a method for treating a patient suffering from osteoarthritis in the knee using an implantable brace that functions as a wedge in the meniscal space to distract or pry open the joint where there has been unicompartment articulate cartilage narrowing, while enabling motion of the knee both in anterior and posterior rolling motions, and providing for rotational and sagittal plane motion.

THE DRAWINGS

FIG. 1 is a side sectional view along the line 1-1 of FIG. 2 showing the femoral and tibial components of a brace in accordance with the invention;

FIG. 2 is a front view of the brace;

DETAILED DESCRIPTION

Figure 3:
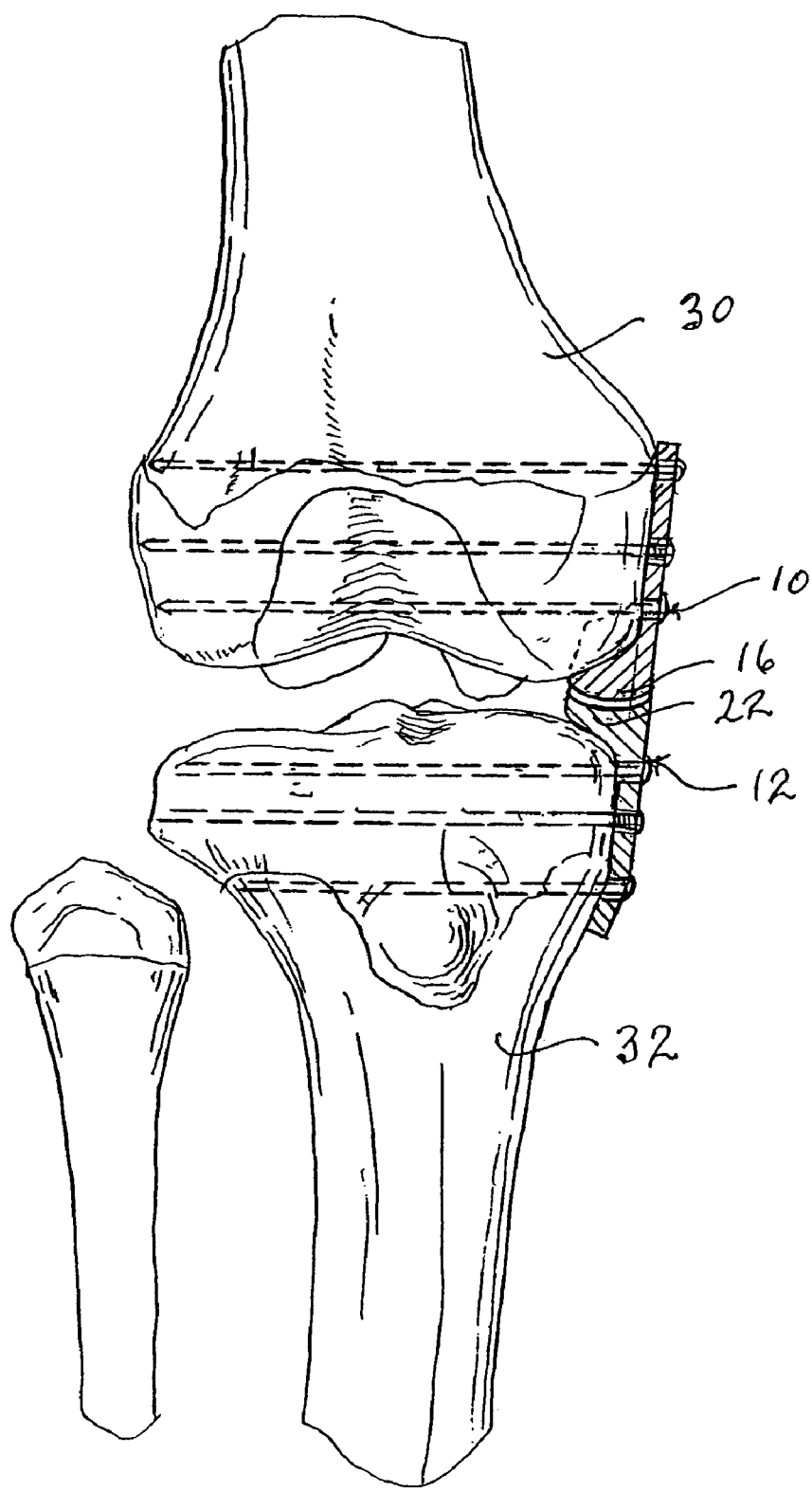
FIG. 3 is a front view of a knee joint showing the brace installed in the medial joint.

A brace according to the invention comprises a femoral component 10 and a tibial component 12. The femoral component 10 includes an elongated stem 14 and a condylar protrusion 16 which has a convex lower surface 18. As shown, stem 14 is more than twice as long as the protrusion 16 is wide.

The tibial component 12 includes a stem 20 and an upper tray 22 which includes a concave upper surface 24 to receive the mating convex lower surface 18 of the condylar protrusion 16 when the brace is installed. Stem 20 is more than twice as long as upper tray 22 is wide. Each component includes holes 26 for attachment to the knee by means of screws.

Tray 22 of tibial component 12 is contoured to match the contour of the tibial plateau whereas the curvature of the condylar protrusion 16 of femoral component 10 should conform to the curvature of the condyle.

Figure 4:
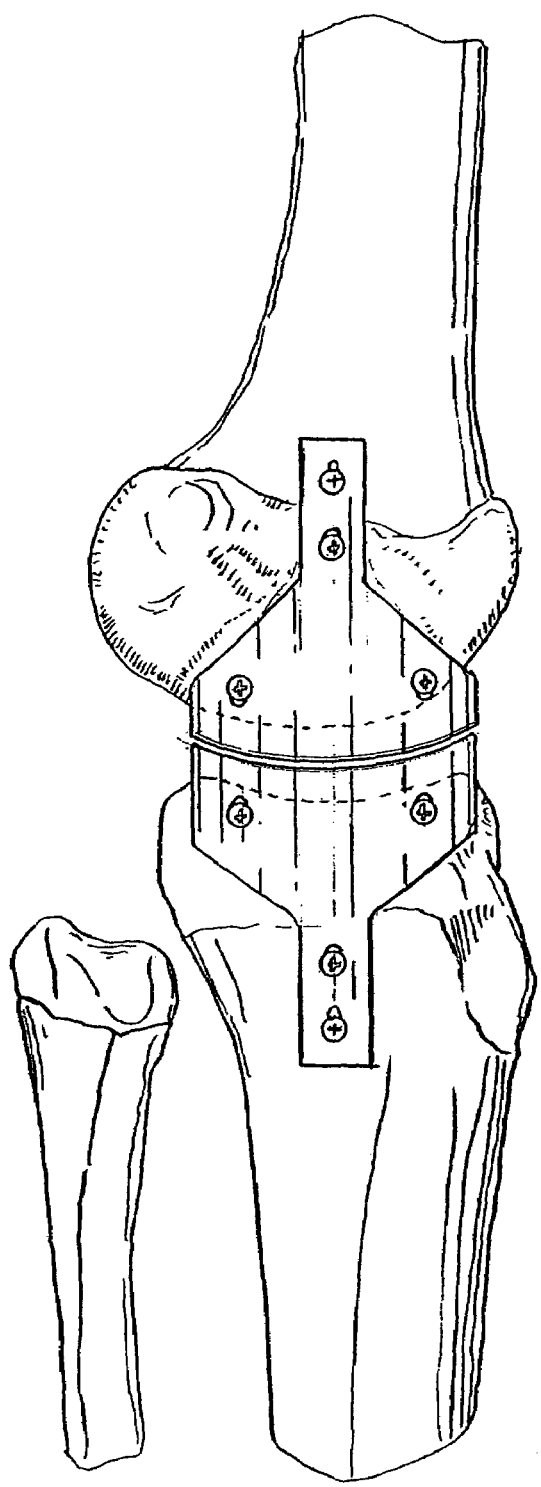
FIG. 4 is a side view of the knee joint shown in FIG. 3.

FIGS. 3 and 4 show the brace installed in the medial joint. Portions of the patient's femur 30 and tibia 32 are removed to receive the stems 14 and 20, respectively. The brace components 10 and 12 are secured by screw fixation underneath the medial collateral ligament (not shown). When installed, the condylar protrusion 16 and tibial tray 22 form a wedge that fits into the triangular meniscal space in the medial joint thereby separating the femur and tibia, with the separation dependent on the thickness of the two components. Because of the complementary curvatures of the engaging surfaces of the condylar protrusion 16 and tibial tray 22, installment of the brace will not impede normal movement of the knee.

The brace may be installed on either the medial or lateral side and serves to distract or decompress a diminished knee compartment of either the medial or lateral joint. In either case, the collateral ligament (medial or lateral) is preserved in introducing the brace to the knee joint.

Enforcement of the brace may require excision of the medial portion of the meniscus or placement of the brace above the meniscal surface. The same type of incision that is used in a unicompartment can be used for insertion of the brace. At the time of surgery, any narrowing of the joint can be determined radiologically and restoration of the joint space can be affirmed by means of X-rays. It is possible that decompression of the medial or lateral joint may result in increased compression on the opposite joint, in which case the use of a brace on both sides of the joint may be indicated.

I claim:

1. An internal brace for distraction arthroplasty, comprising:
   - a femoral component for attachment to a medial or lateral side of a patient's femur near the distal end of the femur, said femoral component including an elongated stem the thickness of which tapers outwardly into a relatively short condylar protrusion having a convex lower surface wherein the upper surface of the condylar protrusion conforms generally to the intact condyle of the patient, the length of the elongated stem being at least twice the width of the condylar protrusion,
   - a tibial component for attachment to a medial or lateral side of a patient's tibia near the proximal end of the tibia, said tibial component including an elongated stem the thickness of which tapers outwardly into a relatively short upper tray having a concave upper surface for engaging the convex lower surface of the condylar protrusion so as to enable relative rotation between the two components wherein the lower surface of the upper tray is contoured to match generally the contour of the patient's intact tibial plateau, the length of the elongated stem of the tibial component being at least twice the width of the short upper tray, and
   - means for attaching the elongated stems of the femoral component and the tibial component to the medial or lateral sides of the patient's intact femur and tibia, respectively, without substantially removing or replacing articular cartilage and with the undersurface of the condylar protrusion engaging the upper surface of the tibial tray, the condylar protrusion and upper tray adapted to be positioned partially in the joint between the patient's intact femur and tibia and functioning to distract the joint.

2. An internal brace according to claim 1, wherein the condylar protrusion and upper tray in combination form a wedge for distracting the joint.

3. An internal brace according to claim 2, wherein the femoral and tibial components are adapted to be attached to the medial side of the patient's knee with the wedge formed by the condylar protrusion and tibial tray adapted to fit into the meniscal space in the patient's medial joint.

4. A pair of internal braces as defined in claim 1, adapted to be placed on both medial and lateral sides of the patient's knee joint.

5. A method for treating a patient suffering from osteoarthritis in the patient's knee joint, comprising the steps of:
   (a) providing an internal knee brace including a femoral component with an elongated stem and a condylar protrusion having a convex bottom surface, and a tibial component with an elongated stem and a concave upper tray for engaging the bottom surface of the condylar protrusion to enable relative rotation between the two components; and
   (b) attaching the elongated stem of the femoral component to the patient's femur adjacent the distal end of the thereof, and attaching the tibial component to the patient's tibia adjacent the proximal end thereof, the elongated stems of the femoral and tibial component being attached underneath the collateral ligament such that the undersurface of the condylar protrusion engages the upper surface of the tibial tray within the meniscal space in the knee joint without substantially removing or replacing articular cartilage in the meniscal space, to distract the patient's knee joint.

6. The method of claim 5, wherein the condylar protrusion and upper tray, in combination, form a wedge distracting said joint.

7. The method of claim 5, further comprising the step of attaching knee braces to both the medial and lateral joints of the patient's knee.

* * * * *